(12) United States Patent
Werner

(10) Patent No.: US 8,597,332 B2
(45) Date of Patent: Dec. 3, 2013

(54) APPARATUS FOR SPINAL-COLUMN STABILIZATION

(75) Inventor: Claudia Werner, Blaustein (DE)

(73) Assignee: Ulrich GmbH & Co. KG, Ulm (DE)

( * ) Notice: Subject to any disclaimer, the term of this patent is extended or adjusted under 35 U.S.C. 154(b) by 280 days.

(21) Appl. No.: 12/388,649

(22) Filed: Feb. 19, 2009

(65) Prior Publication Data

US 2010/0211100 A1   Aug. 19, 2010

(51) Int. Cl.
*A61B 17/70* (2006.01)

(52) U.S. Cl.
USPC .......................................... 606/277; 606/278

(58) Field of Classification Search
USPC ................... 606/53, 60, 246, 247, 250–279, 606/300–320, 322, 324–328
IPC ....................................................... A61B 17/70
See application file for complete search history.

(56) References Cited

U.S. PATENT DOCUMENTS

| | | | | |
|---|---|---|---|---|
| 4,653,481 A * | 3/1987 | Howland et al. | ............... | 606/261 |
| 5,024,213 A * | 6/1991 | Asher et al. | .................... | 606/278 |
| 5,030,220 A * | 7/1991 | Howland | ....................... | 606/261 |
| 5,545,164 A * | 8/1996 | Howland | ....................... | 606/250 |
| 5,584,833 A * | 12/1996 | Fournet-Fayard et al. | ... | 606/278 |
| 5,702,393 A * | 12/1997 | Pfaifer | ........................... | 606/328 |
| 5,709,685 A | 1/1998 | Dombrowski et al. | ......... | 606/61 |
| 5,810,817 A * | 9/1998 | Roussouly et al. | ........... | 606/250 |
| 5,989,250 A | 11/1999 | Wagner et al. | .................. | 606/61 |
| 5,997,539 A * | 12/1999 | Errico et al. | .................... | 606/278 |
| 6,123,706 A * | 9/2000 | Lange | ........................... | 606/264 |
| 6,123,707 A * | 9/2000 | Wagner | ........................ | 606/86 A |
| 6,554,831 B1 * | 4/2003 | Rivard et al. | .................... | 606/253 |
| 6,595,992 B1 * | 7/2003 | Wagner et al. | ................. | 606/250 |
| 6,613,050 B1 * | 9/2003 | Wagner et al. | ................. | 606/250 |
| 7,066,938 B2 * | 6/2006 | Slivka et al. | .................... | 606/914 |
| 7,572,278 B2 * | 8/2009 | Suzuki et al. | .................. | 606/266 |
| 7,862,593 B2 * | 1/2011 | Clement et al. | ............... | 606/260 |
| 2002/0095153 A1 * | 7/2002 | Jones et al. | ...................... | 606/61 |
| 2003/0088248 A1 | 5/2003 | Reed | ............................... | 606/61 |
| 2005/0080419 A1 * | 4/2005 | Donath | ........................... | 606/61 |
| 2005/0096653 A1 | 5/2005 | Doubler et al. | ................. | 606/61 |
| 2005/0149023 A1 * | 7/2005 | Ritland | ........................... | 606/61 |
| 2005/0277931 A1 * | 12/2005 | Sweeney et al. | ................ | 606/61 |
| 2006/0116687 A1 * | 6/2006 | Miller et al. | ..................... | 606/73 |
| 2006/0149231 A1 * | 7/2006 | Bray | ............................... | 606/61 |
| 2006/0167455 A1 * | 7/2006 | Clement et al. | ................. | 606/61 |
| 2007/0100339 A1 * | 5/2007 | Clement et al. | ................. | 606/61 |
| 2007/0233066 A1 * | 10/2007 | Rezach | ........................... | 606/61 |
| 2008/0306551 A1 * | 12/2008 | Sanders et al. | ............... | 606/301 |
| 2009/0062861 A1 * | 3/2009 | Frasier et al. | ................. | 606/278 |
| 2009/0287253 A1 * | 11/2009 | Felix et al. | ..................... | 606/278 |

FOREIGN PATENT DOCUMENTS

EP           1254639        11/2002
WO      WO 2004082522     9/2004

* cited by examiner

*Primary Examiner* — Pedro Philogene
*Assistant Examiner* — Lynnsy Schneider
(74) *Attorney, Agent, or Firm* — Andrew Wilford

(57) ABSTRACT

The invention relates to a device for stabilizing the spine, comprising a bone screw (1) having a screw shaft (2) and having a first threaded portion (5) for insertion into the bone, comprising a rod (3) and a connector (4) that may be fixed to the bone screw (1) for the releasable connection of the rod (3) to the bone screw (1). The connector (3) comprises a connector body (9) having a throughgoing hole (10) and a rod seat (11) that is open on one side, into which the rod (3) may be snap fitted.

13 Claims, 3 Drawing Sheets

APPARATUS FOR SPINAL-COLUMN STABILIZATION

FIELD OF THE INVENTION

The invention relates to a device for stabilizing the spinal column and comprising a bone screw with a shaft having a first threaded portion for insertion into the bone, having a rod and a connector that is attachable to the bone screw for connecting the rod to the bone screw in a releasable fashion.

BACKGROUND OF THE INVENTION

In order to restore and guarantee the load-bearing function of the spine in the case of traumatic or degenerative disorders of the spine, it is often necessary to stabilize the spine using a device. One example of such a device may be found in EP 1 254 639 that discloses a bar-screw system comprising bone screws that may be inserted into the vertebrae as anchors for connectors comprising an annular eyelet through which the rod may be slid. This rod is used to interconnect a plurality of vertebrae to form one stable unit, to which end the rod must be guided through the annular eyelets of the plurality of bone screws used. Because initially the bone screws have to be anchored in the vertebrae, the subsequent insertion of the rod through the eyelets of the connector requires a large surgical field.

OBJECT OF THE INVENTION

The object of the invention is to provide a device for stabilizing the spine of the type mentioned above such that manipulation is simplified during the operation.

SUMMARY OF THE INVENTION

This object is attained according to the invention using a device of the type mentioned above in that the connector comprises a connector body having a throughgoing hole and a laterally open rod seat open into which the rod may be snapped using a spring effect.

The use of such a structure of the connector of a bar-screw system is associated with the large advantage that the rod need not be threaded through the individual annular eyelets of the connectors used with a motion in the direction of its longitudinal axis, but instead the rod may be fitted to the bone screw by means of the connector using a lateral movement in the radial direction relative to the longitudinal axis of the bar.

It is advantageous for the rod seat to be formed by two body extensions located opposite one another and forming a locking seat adapted to the circumferential structure of the bar. This structure allows the spring effect desired by the invention to be achieved in a simple manner, in that the body extensions are prestressed toward each other.

It is particularly preferred within the framework of the invention for the body extensions to each comprise at least one web, with the webs limiting the lateral opening width of the rod seat, thus initially forcing a widening of the rod seat upon snapping in of the rod by a spreading of the body extensions that firmly enclose the rod after insertion as a result of the desired spring effect.

In order to simplify insertion of the rod into the locking seat, the invention further provides for the body extensions to be formed on two legs connected to a base part at a spacing from each other. This structure provides the advantage that a large material thickness may be provided for the connector body with a correspondingly high load capacity without interfering with the deflectability of the body extensions because the deflectability of the body extensions and legs may be utilized in a cumulative fashion.

If the throughgoing hole is formed as a longitudinal bore in the connector body, an improved adjustability of the connector, and therefore of the rod, is possible relative to the bone screw. In such a case, it is preferred for the longitudinal bore to be formed in the legs and to have flanks running at an incline to the longitudinal axis of the connector that then serve as stops for the bone screw in limiting angular movement.

In the context of the invention, it is particularly preferred for the connector to be formed as a coupling for connecting a repositor. Namely, the requirement often arises in the course of a spine operation that not only the vertebrae require stabilization as part of the spine, but it is also necessary to align the vertebrae relative to one another in order to emulate the desired natural anatomic curvature of the spine or to correct a lateral curvature. Configuring the connector as a coupling element for connecting a repositor has the advantage that the bone screws already placed in the vertebrae may be used to effect the orientation of the vertebrae with the aid of the connector by means of the repositor; as a result of this bar-screw system, the orientation thus achieved may be permanently fixed, providing a very simple system with few components, with multiple uses of an application of the connector during operation as a coupling element to the repositor and as part of the bar-screw system in the device for stabilizing the spine.

Taking into account the twistability of the connector around its longitudinal axis through the longitudinal bore by means of the longitudinal bore formed in the connector body, it is useful for the structures for connecting the repositor not to impede the corresponding rotatability of the connector body. This is achieved in that the connector has an annular groove running in the circumferential direction on the connector body for the purpose of cooperating with the repositor.

Furthermore, it is advantageous for the bone screw to have a shaft collar adjacent the first threaded portion because this shaft collar may be used to establish a particular position for the connector relative to the axis of the bone screw, rendering it unnecessary for the connector to support itself directly on the vertebra.

Moreover, the invention further provides for a second threaded portion to be formed on the screw shaft and for a fixing means for cooperating with the second threaded portion to supplement the device for stabilizing the spine because, as a result of the cooperation between the fixing nut and the second threaded portion, it is possible to fix the position of the connector relative to the bone screw and to clamp the rod in the rod seat. In this context, the fact that a washer is provided, having one side adapted to the circumferential shape of the connector body and one side intended to rest against the fixing nut, serves an improved transmission of force.

In the context of the invention, it has further been shown to be advantageous for the screw shaft to have at least one slot splitting the screw shaft into halves in the region of the second threaded portion because, in this manner, it becomes possible to shorten the second threaded portion in a simple fashion to correspond to requirements in order to prevent regions of the bone screw from protruding far past the fixing nut. Alternately or additionally, it is possible for at least one target break point to be formed in the region of the second threaded portion.

In the context of the invention, it is desirable for a preliminary securing of the rod to be present in the rod seat, even independently of a force exerted by the fixing nut on the connector body, such that the surface of the rod seat and/or of the rod advantageously has structures and/or coatings enhancing the retention effect. Corresponding structures may, for example, be formed by longitudinal, transverse, or cross grooves that effect an engagement of abutting surfaces or at least a form fit by means of an increased contact pressure or corresponding edges or knobs.

The invention further relates to a combination of a device for stabilizing the spine, comprising a bone screw, a bar, and a connector having a repositor, with the connector being formed as a coupling element for connecting the repositor, in that the connector has an annular groove running in the circumferential direction on the connector body for cooperating with a notch of the repositor open on one end.

BRIEF DESCRIPTION OF THE DRAWING

The invention shall be described in greater detail in the following with reference to an illustrated embodiment shown in the drawings, in which.

DETAILED DESCRIPTION

Figure 1:
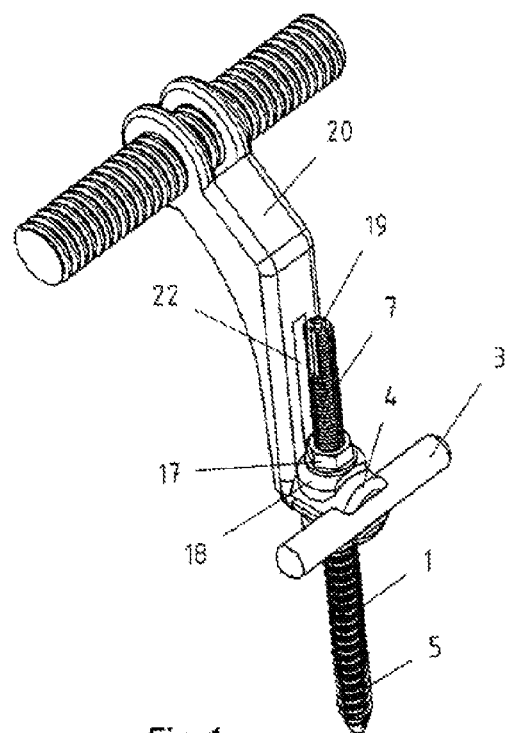
FIG. 1 is a perspective view of the device according to the invention.

The drawing shows a device for stabilizing the spinal column comprising a bar-screw system composed of a bone screw 1 having a screw shaft 2, a rod 3, and a connector 4.

Figure 5:
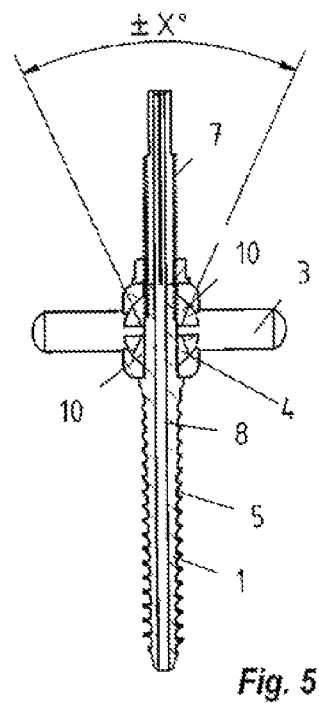
FIG. 5 is section V-V from FIG. 4.
Figure 8:
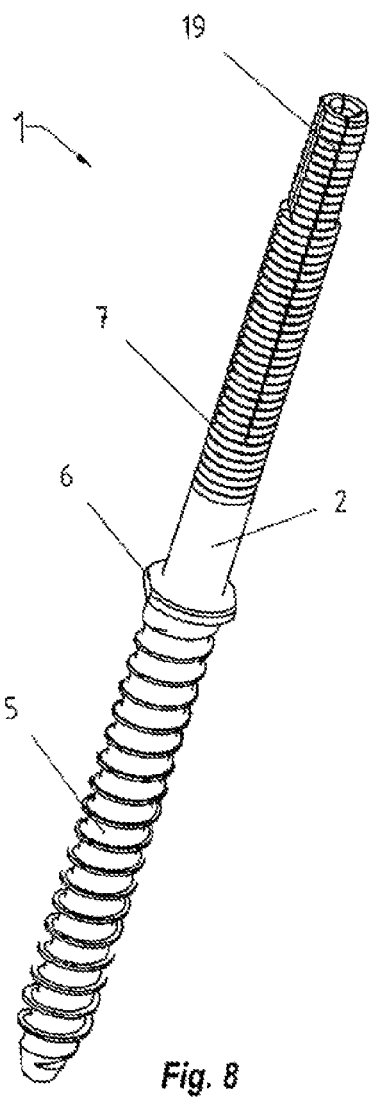
FIG. 8 is a perspective view of only the bone screw.

FIG. 8 shows only the bone screw 1 with a first threaded portion 5 for insertion into the bone. A shaft collar 6 is located adjacent the first threaded portion 5 and a second threaded portion 7 is formed on the end of the screw shaft 2 of the bone screw 1 opposite the first threaded portion 5. A groove 8 for cannulation runs along the screw shaft (FIG. 5).

Figure 9:
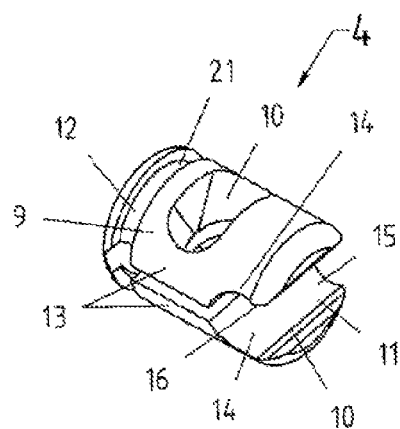
FIG. 9 is a perspective view of only the connector.

In the course of an operation for stabilizing the spine, the invention provides for the first threaded portions 5 of a plurality of such bone screws 1 to be set in the vertebrae of a spine. A connector 4 may then be placed on the shaft collar 6 of each of the bone screws 1, the connectors each having a connector body 9 having a throughgoing hole 10 and a transversely open rod seat 11 into which the rod 3 may be snap fitted. FIG. 9 shows such a connector 4 whose connector body 9 comprises a base part 12 and two legs 13 extending therefrom at a spacing from one another and having outer ends 14 that form the locking seat 15 adapted to the shape of the rod 3, each connected by a respective web 16.

Figure 6:
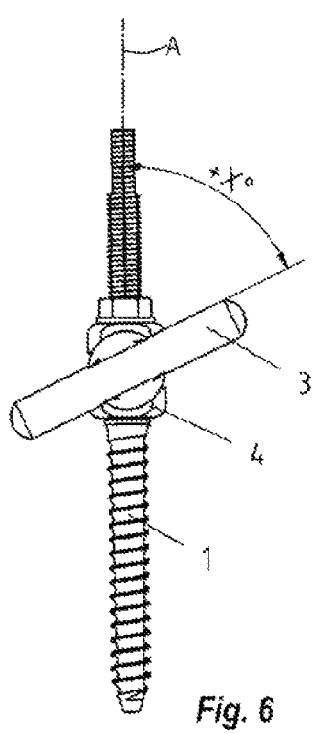
FIG. 6 is a front view of the bar-screw system of FIG. 4 having a connector that has been twisted relative to the longitudinal axis of the screw.
Figure 7:
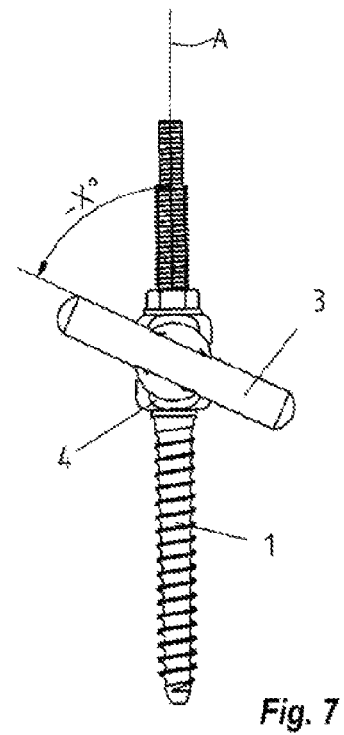
FIG. 7 is a view like FIG. 6 with a connector that has been twisted in the other direction relative to the longitudinal axis of the screw.
Figure 11:
FIG. 11 is a perspective view of only the fixing nut.
Figure 10:
FIG. 10 is a perspective view of only the washer.

FIG. 9 also shows that the throughgoing hole 10 in the connector body 9 is elongated as a slot having flanks inclined relative to the longitudinal axis A of the connector 4, resulting in the possibility of twisting the connector 4 about its longitudinal axis on the screw shaft 2 within limits defied by the flanks as stops. The corresponding adjustability of the connector 4 relative to the bone screw 1 is shown in FIGS. 6 and 7. After the corresponding positioning of the connector 4 on the screw shaft 2 of the bone screw 1 and orienting of the connector 4 relative to the bone screw 1, the rod 3 may be snapped into the rod seat 11; the configuration of the bar-screw system thus achieved may be fixed in place by means of a fixing nut 17 (FIG. 11) screwed onto the second threaded portion 7 of the bone screw 1, optionally with the aid of a washer 18 (FIG. 10). The washer 18 has one side that is shaped to fit complementarily with the connector 4 and a second side intended to abut the fixing nut 17. The screw shaft 2 may be shortened using a break point or a slot 19 formed in the region of the second threaded portion 7.

Figure 2:
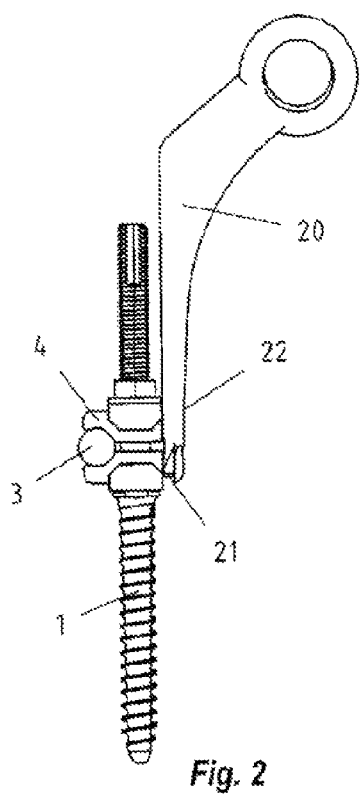
FIG. 2 is a side view of the device according to FIG. 1.
Figure 3:
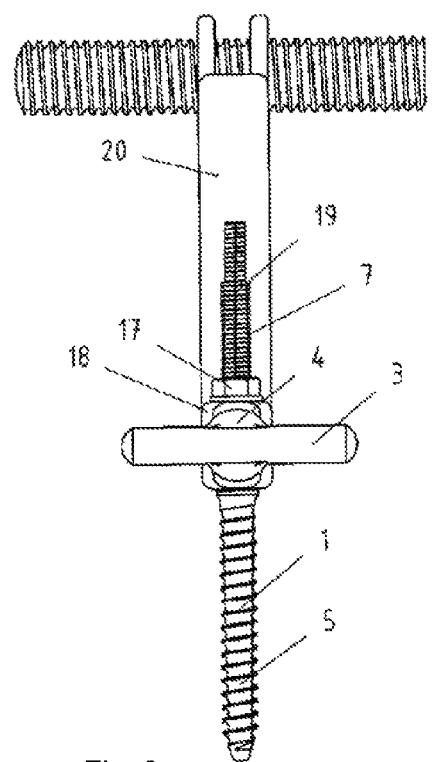
FIG. 3 is a front view of the device according to FIG. 1.
Figure 4:
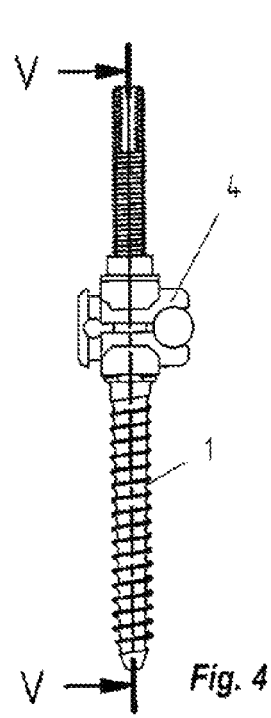
FIG. 4 is a side view of the bar-screw system after the removal of the repositor.

However, the device according to the invention also provides the opportunity for the connector to be initially used to achieve a correct orientation and positioning of the vertebra in the spine before positioning the rod 3 in the rod seat 11 of the connector 4, to this end the connector 4 is formed as shown in FIGS. 1-3 as a coupling formation for connecting a repositor 20 by means of an annular groove 21 formed on the connector body 9 around the base part 12. The repositor 20 is formed with a groove 22 that can be fitted with this annular groove 21 and that is used to effect the change in the position of the spine by the application of corresponding leverage forces by way of the bone screw 1. After the successful repositioning, the orientation of the spine thus achieved may be fixed in place with the bone screw by installation of the bar 3, which is optionally bent, such that the repositor 20 may then be removed from the connector 4 that is acting as a coupling element.

The invention claimed is:

1. A system for stabilizing a spine, the system comprising:
 a plurality of bone screws each extending along a respective axis and having a first threaded portion for insertion into a respective vertebra of a spine;
 a respective connector traversed by each of the screws and formed with
  a body formed with a throughgoing longitudinal bore through which the respective screw extends and opening at slots having flanks inclined to the respective longitudinal axis such that the connector can be tipped relative to the respective screw, and
  a pair of elastically deflectable legs projecting radially from one side of the body and defining a seat open generally radially in one direction away from the respective screw and of a predetermined shape;
 a rod of a shape complementary to the seat and engageable radially inwardly of the screw axes into all of the seats with elastic deflection of the legs away from each other, the rod being elastically gripped between the legs of the connectors when engaged by the seats; and
 respective fastening means for fixing each of the connectors on the respective screw and for pressing together the legs of each of the connectors to clamp them to the rod; and
 a repositor, the connectors each being formed on the other side of the respective bore with an annular groove for connecting with a groove of the repositor that is open at one end.

2. The system defined in claim 1 wherein the legs of each of the connectors form the throughgoing longitudinal bore through which the respective screw extends, the screws each being formed with a respective second threaded portion, the fastening means including
 an anchor collar on each screw, the connectors each sitting on the respective collar at the respective threaded portion, and a nut threaded on each of the second threaded portion and clamping the respective connector against the respective collar.

3. The system defined in claim 2, wherein each connector is U-shaped with the body and the respective annular groove to one side of the respective screw and the two legs formed with the throughgoing longitudinal bore extending diametrally across the respective screw and the seat open radially of the screw on an opposite side of the screw.

4. The system according to claim 2, wherein at least one target break point is formed in the region of each of the second threaded portions.

5. The system according to claim 1, wherein the legs are connected to the body at a spacing from each other.

6. The system according to claim 1, wherein the bone screw comprises a shaft collar adjacent the first threaded portion.

7. The system according to claim 1, wherein a second threaded portion is formed on the screw shaft.

8. The system according to claim 7, wherein the fastening means are each a fixing nut cooperating with the respective second threaded portion.

9. The system according to claim 8, further comprising respective washers each having one side that fits complementarily with the respective connector body and another side intended to abut the respective fixing nut.

10. The system according to claim 7, wherein the screw shaft has at least one slot splitting the screw shaft along the second threaded portion.

11. The system according to claim 1, wherein a surface of the rod seat or of the rod has structures or coatings that increase a retention effect.

12. A system for stabilizing a spine, the system comprising:
a plurality of bone screws each extending along a respective axis and having a first threaded portion for insertion into a respective vertebra of a spine;
a respective connector traversed by each of the screws and formed with
a body formed with a throughgoing longitudinal bore through which the respective screw extends and opening at slots having flanks inclined to the respective longitudinal axis such that the connector can be tipped relative to the respective screw, and
a pair of elastically deflectable legs projecting radially from one side of the body and defining a seat open generally radially in one direction away from the respective screw and of a predetermined shape;
a rod of a shape complementary to the seat and engageable radially inwardly of the screw axes into all of the seats with elastic deflection of the legs away from each other, the rod being elastically gripped between the legs of the connectors when engaged by the seats, the slots being elongated parallel to each other such that the connectors can be tipped only about an axis substantially perpendicular to the screw and to the rod; and
respective fastening means for fixing each of the connectors on the respective screw and for pressing together the legs of each of the connectors to clamp them to the rod; and
a repositor, the connectors each being formed on the other side of the respective bore with a coupling formation for connecting the repositor.

13. The system according to claim 12, wherein the coupling formation is an annular groove on the connector body for cooperating with a groove of the repositor that is open on one end.

* * * * *